United States Patent [19]

Ruddy et al.

[11] Patent Number: 5,424,056

[45] Date of Patent: * Jun. 13, 1995

[54] X-RAY CONTRAST COMPOSITIONS CONTAINING IODOANILINE DERIVATIVES AND PHARMACEUTICALLY ACCEPTABLE CLAYS

[75] Inventors: Stephen B. Ruddy, Schwenksville; Gregory L. McIntire, West Chester; Mary E. Roberts, Downingtown; Thomas J. Caulifield, Audubon; Eugene R. Cooper, Berwyn, all of Pa.

[73] Assignee: Sterling Wintrhop Inc., New York, N.Y.

[*] Notice: The portion of the term of this patent subsequent to Jul. 19, 2011 has been disclaimed.

[21] Appl. No.: 236,287

[22] Filed: Apr. 29, 1994

Related U.S. Application Data

[63] Continuation-in-part of Ser. No. 201,731, Feb. 25, 1994, which is a continuation-in-part of Ser. No. 24,714, Mar. 1, 1993, Pat. No. 5,330,740.

[51] Int. Cl.⁶ .................... A61K 49/04; G01N 21/00
[52] U.S. Cl. .................... 424/9.45; 564/218; 564/442; 424/9.44
[58] Field of Search .................... 424/5; 564/218, 442

[56] References Cited

U.S. PATENT DOCUMENTS

| | | | |
|---|---|---|---|
| 2,820,814 | 1/1958 | Ginsberg | 260/471 |
| 2,832,722 | 8/1958 | Singher | 167/95 |
| 3,360,436 | 12/1967 | Felder et al. | 167/95 |
| 3,666,803 | 5/1972 | Holtermann | 424/5 |
| 3,733,397 | 5/1973 | Bjork et al. | 424/5 |
| 3,795,698 | 3/1974 | Soulal et al. | 260/471 R |
| 4,001,323 | 1/1977 | Felder et al. | 260/559 A |
| 4,069,306 | 1/1978 | Rothman | 424/4 |
| 4,120,946 | 10/1978 | Quemille et al. | 424/4 |
| 4,927,624 | 5/1990 | Bryant et al. | 424/9 |
| 5,019,370 | 5/1991 | Jay et al. | 424/4 |
| 5,107,842 | 4/1992 | Levene et al. | 128/662.02 |
| 5,310,537 | 5/1994 | Illig et al. | 424/5 |
| 5,318,768 | 6/1994 | Illig et al. | 424/5 |
| 5,330,740 | 7/1994 | Illig et al. | 424/5 |

Primary Examiner—Richard L. Raymond
Attorney, Agent, or Firm—Fish & Richardson

[57] ABSTRACT

Disclosed are x-ray contrast compositions for oral or retrograde examination of the gastrointestinal tract comprising an iodoaniline derivative as the x-ray producing agent in combination with a pharmaceutically acceptable clay in a pharmaceutically acceptable carrier; and methods for their use in diagnostic radiology of the gastrointestinal tract.

20 Claims, No Drawings

X-RAY CONTRAST COMPOSITIONS CONTAINING IODOANILINE DERIVATIVES AND PHARMACEUTICALLY ACCEPTABLE CLAYS

This application is a continuation-in-part of application Ser. No. 08/201,731 filed on Feb. 25, 1994, which in turn is a continuation-in-part of application Ser. No. 08/024,714 filed on Mar. 1, 1993, now U.S. Pat. No. 5,330,740.

BACKGROUND OF THE INVENTION

1. Field of the Invention

This invention relates to x-ray contrast compositions containing iodoaniline derivatives and a pharmaceutically acceptable clay and methods for their use in diagnostic radiology of the gastrointestinal tract.

2. Reported Developments

Roentgenographic examination utilizing X-rays and computed tomography (hereinafter CT) scans of fractures and other conditions associated with the skeletal system is routinely practiced without the use of contrast agents. X-ray visualization of organs containing soft tissue, such as the gastrointestinal (hereinafter GI) tract, requires the use of contrast agents which attenuate X-ray radiation. D. P. Swanson et al in "Pharmaceuticals In Medical Imaging", 1990, MacMillan Publishing Company, provides an excellent background in medical imaging utilizing contrast agents and compositions therewith.

Roentgenographic examination of the GI tract are indicated for conditions of digestive disorders, changes in bowel habit, abdominal pain, GI bleeding and the like. Prior to radiological examination, administration of a radiopaque contrast medium is necessary to permit adequate delineation of the respective lumen or mucosal surface from surrounding soft tissues. Accordingly, a contrast medium is administered orally to visualize the mouth, pharynx, esophagus, stomach, duodenum and proximal small intestine. The contrast medium is administered rectally for examination of the distal small intestine and the colon.

The most widely used contrast agent for the visualization of the GI tract is barium sulfate administered as a suspension orally or rectally as an enema. (See, for example, U.S. Pat. Nos.: 2,659,690; 2,680,089; 3,216,900; 3,235,462; 4,038,379 and 4,120,946) Notwithstanding its relatively good contrast characteristics, negligible absorption from the GI tract following oral or rectal administration and speedy excretion from the body, barium sulfate has certain disadvantages. In the presence of intestinal fluids it lacks homogeneity and poorly adheres to mucus membranes which can result in poor X-ray images. In the colon, when administered as an enema, it flocculates and forms irregular clumps with fecal matter.

Iodinated organic compounds have also been used as GI contrast agents since the iodine atom is an effective X-ray absorber. They have the most versatility and are utilized in the widest variety of procedures. They are very absorptive of X-rays with which the iodine interacts and produce a so-called photoelectric effect which is a large magnification in contrast caused by the photons stopped in the iodine-containing medium. The magnification of contrast exceeds the level that would be expected from relative changes in density. Because of this magnification, relatively low concentrations of the contrast agent can be utilized. (For iodinated agents see, for example, U.S. Pat. Nos.: 2,786,055; 3,795,698; 2,820,814; 3,360,436; 3,574,718, 3,733,397; 4,735,795 and 5,047,228.)

The desiderata for an ideal GI contrast agent includes: good toxicological profile; the ability to fill the entire bowel/lumen and evenly coat the gut mucosa so that the presence of the bowel is detectable when the lumen is not distended; and nonirritation to the intestinal mucosa; and passage through the GI tract without producing artifacts or stimulating vigorous intestinal peristalsis.

These requirements were addressed by many investigators and their efforts resulted in great improvements over the years. The requirement of evenly coating the gut mucosa with a contrast agent to effectively cover the walls of the intestines proved to be rather difficult. Without meeting these requirements it is impossible to obtain X-ray pictures of high precision. To that end, the use of certain polymer additives were proposed as illustrated hereunder.

U.S. Pat. No. 4,069,306 discloses an x-ray contrast preparation which is said to adhere to the walls of body cavities. The preparation comprises a finely divided water-insoluble inorganic x-ray contrast agent and minute particles of a hydrophilic polymer which is insoluble in water but is water-swellable. The body cavity is supplied with such preparation suspended in water. The x-ray contrast agent is present in admixture with and/or enclosed in and/or adhered to said minute polymer particles.

U.S. Pat. No. 4,120,946 discloses a pharmaceutical composition for barium opacification of the digestive tract, comprising colloidal barium sulfate and a polyacrylamide in an aqueous vehicle. The polyacrylamide forms a viscous solution at low concentration which makes it possible to maintain the barium sulfate in suspension and at the same time permit good adherence of the preparation to the walls of the organ which it is desired to x-ray.

U.S. Pat. No. 5,019,370 discloses a biodegradable radiographic contrast medium comprising biodegradable polymeric spheres which carry a radiographically opaque element, such as iodine, bromine, samarium and erbium. The contrast medium is provided either in a dry or liquid state and may be administered intravenously, orally and intra-arterially.

While these polymeric materials greatly enhance attachment of the contrast agent used therewith to the walls of organs for better visualization thereof, there is still a need for an improved x-ray imaging medium that uniformly coats the soft tissues subjected to diagnostic x-ray examination.

We have now discovered that the use of certain natural clays in combination with an x-ray producing agent enhance the uniformity of coating on the gastrointestinal tract and the quality of x-ray images. In addition, these clays mask the unpleasant odor and taste of the x-ray contrast formulations as well as enhance the physical stability thereof.

SUMMARY OF THE INVENTION

It is the object of the present invention to provide compositions for coating the gastrointestinal tract of mammals to form an effective radiopaque coating thereon by which diagnostic examination of the GI tract may be accomplished. To that end, a thin coating is formed on the inner surface of the GI tract effected by ingesting, prior to visualization by an x-ray emitting device, a composition containing a pharmaceutically acceptable clay and an x-ray contrast agent. Such compositions must meet several requirements: both the x-ray contrast agent and the clay must be nontoxic; must not contain leachable or digestible components that would deleteriously affect the patient; and no components of the coating should be absorbed by, and pass through, the inner surface of the intestine.

The contrast agent and the pharmaceutically acceptable clay are incorporated in a liquid media for administration to a mammal for x-ray visualization of the GI tract.

The x-ray contrast agent of the present invention is of the formula:

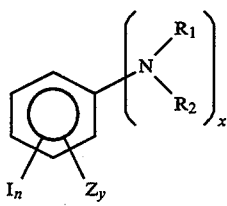

or a pharmaceutically acceptable salt thereof wherein

Z is H, halo, $C_1$–$C_{20}$ alkyl, cycloalkyl, lower alkoxy, cyano, where the alkyl and cycloalkyl groups can be substituted with halogen or halo-lower-alkyl groups;

$R_1$ and $R_2$ are independently H, $C_1$–$C_{25}$ alkyl, cycloalkyl, acetyl or halo-lower-alkyl, wherein said $C_1$–$C_{25}$ alkyl, cycloalkyl and halo lower-alkyl are optionally substituted with fluoro-lower-alkyl, aryl, lower-alkoxy, hydroxy, carboxy, lower-alkoxy carbonyl or lower-alkoxy-carbonyloxy and said acetyl is optionally substituted with fluoro-lower-alkyl, aryl, lower-alkoxy, hydroxy, lower-alkoxy carbonyl or lower-alkoxy-carbonyloxy;

n is 1–4;

y is 1–4; and x is 1 or 2.

As used herein, the term halogen (or halo) means fluorine, chlorine, bromine or iodine.

As used herein, the term cycloalkyl means carbocyclic rings having from three to eight ring carbon atoms including cyclopropyl, cyclobutyl, cyclopentyl, cyclohexyl and cyclooctyl which may be substituted on any ring carbon atom thereof by one or more lower-alkyl groups, lower-alkoxy groups or halogens.

As used herein the terms lower-alkyl and lower-alkoxy mean monovalent aliphatic radicals, including branched chain radicals, of from one to ten carbon atoms. Thus, the lower-alkyl moiety of such groups include, for example, methyl, ethyl, propyl, isopropyl, n-butyl, sec-butyl, t-butyl, n-pentyl, 2-methyl-3-butyl, 1-methylbutyl, 2-methylbutyl, neopentyl, n-hexyl, 1-methylpentyl, 3-methylpentyl, 1-ethylbutyl, 2-ethylbutyl, 2-hexyl, 3-hexyl, 1,1,3,3-tetramethylpentyl, 1,1-dimethyloctyl and the like.

As used herein, the term aryl means an aromatic hydrocarbon radical having six to ten carbon atoms. The preferred aryl groups are phenyl, substituted phenyl and naphthyl substituted by from one to three, the same or different members of the group consisting of lower-alkyl, halogen, hydroxy-lower-alkyl, alkoxy-lower-alkyl and hydroxy.

The x-ray contrast compound can comprise one, two, three or four iodine atoms per molecule; preferred species contain at least two, and more preferably, at least three iodine atoms per molecule.

The solid x-ray contrast agents in particulate forms useful in the practice of the present invention can be prepared by techniques known in the art. The solid agents are comminuted to the desired size using conventional milling methods, such as airjet or fragmentation milling. We have found that an effective average particle size of less than about 100μ provides for good distribution and coating in the GI tract. As used herein, particle size refers to a number average particle size as measured by conventional techniques, such as sedimentation field flow fractionation and disk centrifugation. An effective average particle size of less than about 100μ means that at least about 90% of the particles have a weight average particle size of less than about 100μ as measured by art recognized techniques.

The compositions may be in the form of dispersions or suspensions when the x-ray contrast agents is a solid, or emulsions when the x-ray contrast agent is an oil; we prefer to use emulsions as the preferred embodiment.

The natural clays incorporated in the compositions of the present invention are selected from the group consisting of montmorillonite, beidelite, nontronite, hectorite and saponite.

A method for diagnostic imaging of the GI tract for use in medical procedures in accordance with this invention comprises orally or rectally administering to the mammalian patient in need of x-ray examination, an effective contrast producing amount of a composition of the present invention. After administration, at least a portion of the GI tract containing the administered composition is exposed to x-rays to produce an x-ray image pattern corresponding to the presence of the contrast agent, then the x-ray image is visualized and interpreted using techniques known in the art.

DETAILED DESCRIPTION OF THE INVENTION

Compounds of the present invention can be made according to the procedure known in the art using commercially available starting materials, intermediates and reagents. Starting materials, reagents and solvents can be obtained from chemical suppliers such as Aldrich, Baker and Eastman Chemical Companies, or they may be prepared by techniques known in the art.

The following examples will further illustrate the compounds used in the present invention.

EXAMPLE 1

N-acetyl-N-2-octyl-4-iodoaniline

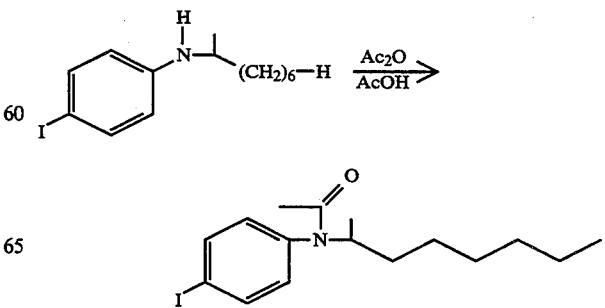

A flask containing N-(4'-iodophenyl)-2-amino octane (1.50 g, 4.5 mmol) was charged with acetic acid (15 ml) and acetic anhydride (15 ml). The reaction flask was immersed in an oil bath which was warmed to 70° C. over a period of 0.5 hr. After stirring for 19 hrs, the reaction was allowed to cool, diluted with ether (200 ml), washed with water (2×50 ml), saturated aqueous sodium bicarbonate (4×50 ml), water (2×50 ml) and brine (50 ml), dried ($Na_2SO_4$), filtered, and evaporated in vacuo. Flash column chromatography (silica, 1:4; EtOAc:hexanes) provided N-acetyl-N-2-octyl-4-iodoaniline (1.48 g, 70%) as a white solid. Mp 60°–62° C.

Title Compound: $^1H$ (300 MHz) and $^{13}C$ (75 MHz) NMR spectra were consistent with the desired structure. FAB/MS MH+ 374. Calculated for $C_{16}H_{24}NIO$: C, 51.48; H, 6.48; N, 3.75; I, 34.00. Found: C, 51.68, H, 6.46; N, 3.67; I, 33.87.

EXAMPLE 2

N-(4'-iodophenyl)-2-aminooctane

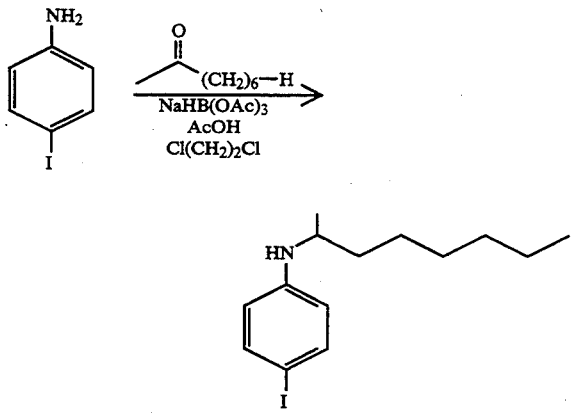

A flask containing 4-iodoaniline (11.0 g, 50.2 retool) was charged with dry dichloroethane (125 ml), 2-octanone (7.9 ml, 50.0 retool) and sodium triacetexyborohydride (13.8 g, 65 retool). After stirring for 10 minutes, acetic acid (2.9 ml, 50.7 retool) was added via syringe over a 5 minute period. The reaction was stirred under an $N_2$ atmosphere for 16 hrs. At the end of this period the reaction was quenched by the careful addition of a solution of saturated aqueous ammonium chloride (100 ml). After stirring for 0.5 hr, the reaction was poured over ether (250 ml) and the layers were separated. The ether layer was washed with saturated aqueous ammonium chloride (100 ml), dried ($Na_2SO_4$), filtered and evaporated in vacuo. Flash column chromatography (silica, 1:39; EtOAC:hexanes) provided N-(4'-iodophenyl)-2-aminooctane (14.6 g, 88%) as a light yellow oil.

Title Compound: $^1H$ (300 MHz) and 13C (75 MHz) NMR spectra were consistent with the desired structure. Calculated for $C_{14}H_{22}NI$: C, 50.97; H, 6.69; I, 38.31. Found: C, 51.19, H, 6.72; I, 37.94.

The natural, pharmaceutically acceptable clays incorporated in the present invention comprise aluminum silicates. They are used in purified form, suitable for administration to patients. The natural, pharmaceutically acceptable clays of the present invention, generally referred to as smectities, consist of dioctohedral smectites and trioctahedral smectites.

Dioctahedral smectites include:
montmorillonite, having the formula
$M^+Al_{3y}(FeMg)_y Si_4O_{10}(OH)_2 \cdot nH_2O$;
beidelite, having the formula
$M^+(Al_2(Si_{4-x}Al_x)O_{10}(OH)_2 \cdot nH_2O$;
nontronite, having the formula
$M^+(Fe_2{}^{3+}(Si_{4-x}Al_x)O_{10}(OH)_2 \cdot nH_2O$;
wherein $M^+$ is Na, Ca or Mg.
Trioctahedral smectites include:
saponite, having the formula
$M^+(Mg_{3-y}(AlFe)_y) Si_{4-x}Al_x)O_{10}(OH)_2 \cdot nH_2O$; and
hectorite, having the formula
$M^+(Mg_{3-y}Li_y) Si_4O_{10}(OH)_2 \cdot nH_2O$;
wherein $M^+$ is Na, Ca or Mg.

The clays are available from chemical suppliers, such as, for example, American Colloid Company, Arlington Heights, Ill., under the tradenames:
MAGNABRITE®HS;
HECTABRITE®DP,
HECTABRITE®LT,
CARMARGO®White,
POLARGEL®NF,
POLARGEL®HV, and
VOLCLAY®NF-BC.

Other suppliers include: Engelhard Corp., Iselin, N.J.; Ashland Chemical Inc., Colombus, Ohio; RT Vanderbilt Co., Inc., Norwalk, Conn. and Whittaker Clark & Daniels, Inc., S. Plainfield, N.J.

The contrast agent and the pharmaceutically acceptable clay are formulated for administration using physiologically acceptable carriers or excipients in a manner within the skill of the art. The contrast agent with the addition of pharmaceutically acceptable aids (such as surfactants and emulsifiers) and excipients may be suspended or emulsified in an aqueous medium resulting in a suspension or emulsion.

COMPOSITIONS OF THE PRESENT INVENTION

Compositions of the present invention comprise the following pharmaceutically acceptable components based on % w/v:

| Ingredients | Broad Range | Preferred Range | Most Preferred Range |
|---|---|---|---|
| Contrast agent | 5–45 | 10–35 | 15–25 |
| Clay | 0.1–10 | 0.5–5 | 1-2 |
| Surfactant | 1–20 | 2–10 | 3–5 |
| Excipients | 0–15 | 0.5–5 | 1-2 |
| Water-q.s. to 100% by volume | | | |

Excipients contemplated by the present invention include antifoaming agents, such as simethicone, siloxyalkylene polymers and polyoxyalkylated natural oils; preservatives, such as methyl paraben, propyl paraben, benzoic acid and sorbic acid; flavoring/sweetening agents, such as sodium saccharine; and coloring agents, such as lakes and dyes.

While the iodoaniline derivatives of the present invention in formulations with a pharmaceutically acceptable vehicle provide good quality x-ray images, the addition of a pharmaceutically acceptable clay to the formulations greatly increases the quality of the x-ray images. At the low extreme of the concentration range there is little or no benefit gained, while above the higher extreme of the concentration range the formulations are too viscous for administration.

The following formulation examples will further illustrate the invention.

EXAMPLE 3

| Components | |
|---|---|
| N-acetyl-N-2-octyl-4-iodoaniline | 18.00 g |
| HECTABRITE ® DP | 1.5 g |
| Sorbitan Monostearate | 0.5 g |
| Polysorbate 60 (Tween 60) | 1.2 g |
| Poloxamer 338 | 4.0 g |
| Sodium Saccharine | 0.3 g |
| Benzoic Acid | 0.1 g |
| Sorbic Acid | 0.05 g |
| Water q.s. to make 100 ml | |

EXAMPLE 4

| Components | |
|---|---|
| N-(4'-iodophenyl)-2-amino octane | 25.00 |
| POLARGEL ® NF | 2.0 g |
| Sorbitan Mono-oleate | 0.4 g |
| Polysorbate 20 (Tween 20) | 1.2 g |
| Polvinylalcohol | 4.5 g |
| Sodium Saccharine | 0.2 g |
| Simethicone (food-grade) | 0.1 g |
| Water q.s. to make 100 ml | |

The formulations are prepared using standard formulation techniques which are well-known in the pharmaceutical industry.

The surface active agents used in the present invention may be cationic, anionic, nonionic or zwittefionic.

Suitable cationic surfactants include cetyl trimethyl ammonium bromide, cetyl pyridinium chloride, myristyl gamma picolinium chloride and benzalkonium chloride. Suitable anionic agents include sodium lauryl sulphate, sodium heptadecyl sulphate, alkyl benzenesulphonic acids and salts thereof, sodium butylnapthalene sulfonate, and sulphosuccinates. Zwitterionic surface active agents are substances that when dissolved in water they behave as diprotic acids and, as they ionize, they behave both as a weak base and a weak acid. Since the two charges on the molecule balance each other out they act as neutral molecules. The pH at which the zwitterion concentration is maximum is known as the isoelectric point. Compounds, such as certain amino acids having an isoelectric point at the desired pH of the formulations of the present invention are useful in practicing the present invention.

In preparing the formulations of the present invention we prefer to use nonionic emulsifiers or surface active agents which, similarly to the nonionic contrast agents, possess a superior toxicological profile to that of anionic, cationic or zwitterionic agents. In the nonionic emulsifying agents the proportions of hydrophilic and hydrophobic groups are about evenly balanced. They differ from anionic and cationic surfactants by the absence of charge on the molecule and, for that reason, are generally less irritating than the cationic or anionic surfactants. Nonionic surfactants include carboxylic esters, carboxylic amides, ethoxylated alkylphenols, ethoxylated aliphatic alcohols, ethylene oxide polymer or ethylene oxide/propylene oxide co-polymers polyvinylpyrrolidone and polyvinylalcohol.

One particular type of carboxylic ester nonionic surface active agents are the partial, for example mono-, esters formed by the reaction of fatty and resin acids, for example of about 8 to about 18 carbon atoms, with polyalcohols, for example glycerol, glycols such as mono-, di-, tetra- and hexaethylene glycol, sorbitan, and the like; and similar compounds formed by the direct addition of varying molar ratios of ethylene oxide to the hydroxy group of fatty acids.

Another type of carboxylic esters are the condensation products of fatty and resin partial acids, for example mono-, esters ethylene oxide, such as fatty or resin acid esters of polyoxyethylene sorbitan and sorbitol, for example polyoxyethylene sorbitan, mono-tall oil esters. These may contain, for example, from about 3 to about 80 oxyethylene units per molecule and fatty or resin acid groups of from about 8 to about 18 carbon atoms. Examples of naturally occurring fatty acid mixtures which may be used are those from coconut oil and tallow while examples of single fatty acids are dodecanoic acid and oleic acid.

Carboxylic amide nonionic surface active agents are the ammonia, monoethylamine and diethylamine amides of fatty acids having an acyl chain of from about 8 to about 18 carbon atoms.

The ethoxylated alkylphenol nonionic surface active agents include various polyethylene oxide condensates of alkylphenols, especially the condensation products of mono-alkylphenols or dialkylphenols wherein the alkyl group contains about 6 to about 12 carbon atoms in either branched chain or particularly straight chain configuration, for example, octyl cresol, octyl phenol or nonyl phenol, with ethylene oxide, said ethylene oxide being present in amounts equal to from about 5 to about 25 moles of ethylene oxide per mole of alkylphenol.

Ethoxylated aliphatic alcohol nonionic surface active agents include the condensation products of aliphatic alcohols having from about 8 to 18 carbon atoms in either straight chain or branched chain configuration, for example oleyl or cetyl alcohol, with ethylene oxide, said ethylene oxide being present in equal amounts from about 30 to about 60 moles of ethylene oxide per mole of alcohol.

Preferred nonionic surface active agents include:
(a) Sorbitan esters (sold under the trade name Span) having the formula:

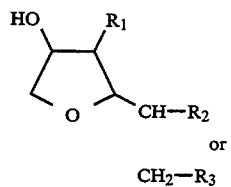

or $CH_2-R_3$ wherein
$R_1=R_2=OH$, $R_3=R$ for sorbitan monoesters,
$R_1=OH$, $R_2=R_3=R$ for sorbitan diesters,
$R_1=R_2=R_3=R$ for sorbitan triesters,
where $R=$
  $(C_{11}H_{23})$ COO for laurate,
  $(C_{17}H_{33})$ COO for oleate,
  $(C_{15}H_{31})$ COO for palmitate,
  $(C_{17}H_{35})$ COO for stearate;
(b) Polyoxyethylene alkyl ethers (i.e. Brijs) having the formula:

$CH_3(CH_2)_x(O-CH_2-CH_2)_yOH$ where $(x+1)$ is the number of carbon atoms in the alkyl chain, typically:

| | |
|---|---|
| 12 lauryl | (dodecyl) |
| 14 myristyl | (tetradecyl) |
| 16 cetyl | (hexadecyl) |
| 18 stearyl | (octadecyl) | and y is the number of ethylene oxide groups in the hydrophilic chain, typically 10–60;

(c) Polyethylene sorbitan fatty acid esters, sold under the trade names of Tween or Polysorbates 20, 40, 60, 65, 80 & 85, having the formulas (1) and (2)

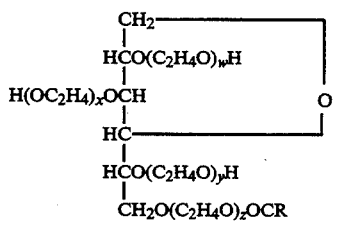

Polyoxyethylene sorbitan monoester

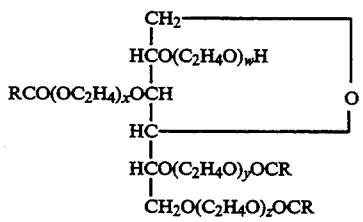

Polyoxyethylene sorbitan triester wherein
w+x+y+z=20 (Polysorbate 20, 40, 60, 65, 80 and 85)
w+x+y+z=5 (Polysorbate 81)
w+x+y+z=4 (Polysorbate 21 and 61);

(d) Polyoxyethylene stearates, such as:
poly(oxy-1,2-ethanediyl), α-hydro-ω-hydroxy-octadecanoate;
polyethylene glycol monostearate; and
poly(oxy-1,2-ethanediyl)-α-(1-oxooctadecyl)-ω-hydroxy-polyethylene glycol monostearate.

(e) Polyethylene oxide/polypropylene oxide block copolymers, sold under the name PLURONIC ™, which include Poloxamer 407 (PLURONIC ™ F127), Poloxamer 188 (PLURONIC ™ F68), Poloxamer 237 (PLURONIC ™ F87) and Poloxamer 338 (PLURONIC ™ F108);

(f) Polyvinylpyrrolidone; and
(g) Polyvinylalcohol.

The dosages of the contrast agent used according to the method of the present invention will vary according to the precise nature of the contrast agent used. Preferably, however, the dosage should be kept as low as is consistent with achieving contrast enhanced imaging. By employing as small amount of contrast agent as possible, toxicity potential is minimized. For most contrast agents of the present invention dosages will be in the range of from about 0.1 to about 16.0 g iodine/kg body weight, preferably in the range of from about 0.5 to about 6.0 g iodine/kg of body weight, and most preferably, in the range of from about 1.2 to about 2.0 g iodine/kg body weight for regular x-ray visualization of the GI tract. For CT scanning the contrast agents of the present invention will be in the range of from about 1 to about 600 mg iodine/kg body weight, preferably in the range of from about 20 to about 200 mg iodine/kg body weight, and most preferably in the range of from about 40 to about 80 mg iodine/kg body weight.

When administered to mammals, the compositions of the present invention produce excellent x-ray and CT images.

The invention, having been fully described, it will be apparent to one skilled in the art that changes and modifications can be made thereto without departing from the spirit and scope thereof.

What is claimed is:

1. An x-ray contrast composition for oral or retrograde examination of the gastrointestinal tract comprising on a % weight per volume basis:

(a) from about 5 to 45% of an x-ray contrast producing agent having the formula, or a pharmaceutically acceptable salt thereof

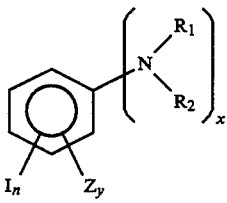

wherein
Z is H, halo, $C_1C_{20}$ alkyl, cycloalkyl, lower alkoxy, cyano, where the alkyl and cycloalkyl groups can be substituted with halogen or halo-lower-alkyl groups;
$R_1$ and $R_2$ are independently H, $C_1$–$C_{25}$ alkyl, cycloalkyl, acetyl or halo-lower-alkyl, wherein said $C_1$–$C_{25}$ alkyl, cycloalkyl and halo lower-alkyl are optionally substituted with fluoro-lower-alkyl, aryl, lower-alkoxy, hydroxy, carboxy, lower-alkoxy carbonyl or lower-alkoxy-carbonyloxy and said acetyl is optionally substituted with fluoro-lower-alkyl, aryl, lower-alkoxy, hydroxy, lower-alkoxy carbonyl or lower-alkoxy-carbonyloxy;
n is 1–4;
y is 1–4; and
x is 1 or 2;

(b) from about 0.1 to 10% of a pharmaceutically acceptable clay selected from the group consisting off montmorillonite, beidelite, nontronite, hectorite and saponite;

(c) from about 1.0 to 20% of a surfactant selected from the group consisting of nonionic, anionic, cationic and zwitterionic surfactants;

(d) from about 0 to 15% of an excipient; and
(e) water to make 100% by volume.

2. The x-ray contrast composition of claim 1 wherein said x-ray contrast producing agent is present in an amount of from about 10 to 35%.

3. The x-ray contrast composition of claim 1 wherein said pharmaceutically acceptable clay constitutes from 0.5 to 5% of the composition.

4. The x-ray contrast composition of claim 1 wherein said surfactant constitutes from 2 to 10% of the composition.

5. The x-ray contrast composition of claim 1 wherein said excipient constitutes from 0.5 to 5% of the composition.

6. The x-ray contrast composition of claim 1 wherein said nonionic surface active agent is selected from the group consisting of carboxylic esters, carboxylic amides, ethoxylated alklyphenols, ethoxylated aliphatic alcohols, ethylene oxide polymer, ethylene oxide/propylene oxide co-polymer, polyvinylpyrrolidone and polyvinylalcohol.

7. The x-ray contrast composition of claim 1 wherein said surfactant is sorbitan ester having the formula:

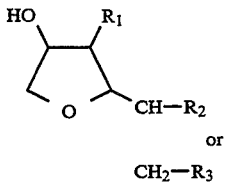

or

CH$_2$—R$_3$ wherein

R$_1$=R$_2$=OH, R$_3$=R for sorbitan monoesters,
R$_1$=OH, R$_2$=R$_3$=R for sorbitan diesters,
R$_1$=R$_2$=R$_3$=R for sorbitan triesters,
where R=
  (C$_{11}$H$_{23}$) COO for laurate,
  (C$_{17}$H$_{33}$) COO for oleate,
  (C$_{15}$H$_{31}$) COO for palmitate or
  (C$_{17}$H$_{35}$) COO for stearate.

8. The x-ray contrast composition of claim 1 wherein said surface active agent is polyoxyethylene stearate.

9. The x-ray contrast composition of claim 1 wherein said surfactant is polyoxyethylene sorbitan fatty acid ester of the formulas (1) and (2)

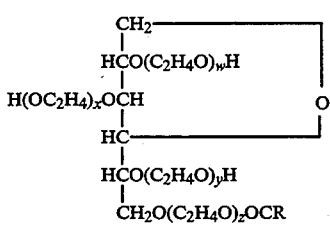

Polyoxyethylene sorbitan monoester

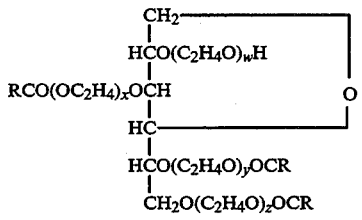

Polyoxyethylene sorbitan triester wherein
w+x+y+z =20
w+x+y+z =5
w+x+y+z =4,

10. The x-ray contrast composition of claim 1 wherein said x-ray contrast producing agent is selected from the group consisting of: N-acetyl-N-2-octyl-4-iodoaniline or N-(4'-iodophenyl)-2-amino octane.

11. A method of carrying out x-ray examination of the gastrointestinal tract of a patient, said method comprises the oral or rectal administration to the patient an x-ray contrast formulation comprising:

(a) from about 5 to 45% of an x-ray contrast producing agent having the formula, or a pharmaceutically acceptable salt thereof

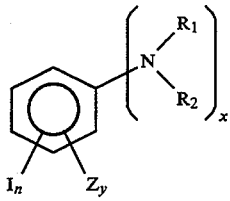

wherein

Z is H, halo, C$_1$–C$_{20}$ alkyl, cycloalkyl, lower alkoxy, cyano, where the alkyl and cycloalkyl groups can be substituted with halogen or halo-lower-alkyl groups;

R$_1$ and R$_2$ are independently H, C$_1$–C$_{25}$ alkyl, cycloalkyl, acetyl or halo-lower-alkyl, wherein said C$_1$–C$_{25}$ alkyl, cycloalkyl and halo lower-alkyl are optionally substituted with fluoro-lower-alkyl, aryl, lower-alkoxy, hydroxy, carboxy, lower-alkoxy carbonyl or lower-alkoxy-carbonyloxy and said acetyl is optionally substituted with fluoro-lower-alkyl, aryl, lower-alkoxy, hydroxy, lower-alkoxy carbonyl or lower-alkoxy-carbonyloxy;

n is 1–4;
y is 1–4; and
x is 1 or 2;

(b) from about 0.1 to 10% of a pharmaceutically acceptable clay selected from the group consisting of: montmorillonite, beidelite, nontronite, hectorite and saponite;

(c) from about 1.0 to 20% of a surfactant selected from the group consisting of nonionic, anionic, cationic and zwitterionic surfactants;

(d) from about 0.0 to 15% of an excipient; and (e) water to make 100% by volume.

12. The method of claim 11 wherein said x-ray contrast producing agent is present in an amount of from about 10 to 35%.

13. The method of claim 11 wherein said pharmaceutically acceptable clay constitutes from 0.5 to 5% of the composition.

14. The method of claim 11 wherein said surfactant constitutes from 2 to 10% of the composition.

15. The method of claim 11 wherein said excipient constitutes from 0.5 to 5% of the composition.

16. The method of claim 11 wherein said nonionic surface active agent is selected from the group consisting of carboxylic esters, carboxylic amides, ethoxylated alklyphenols, ethoxylated aliphatic alcohols, ethylene oxide polymer, ethylene oxide/propylene oxide co-polymer, polyvinylpyrrolidone and polyvinylalcohol.

17. The method of claim 11 wherein said surfactant is sorbitan ester having the formula:

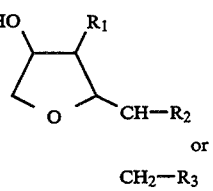

or

CH$_2$—R$_3$ wherein $R_1=R_2=OH$, $R_3=R$ for sorbitan monoesters, $R_1=OH$, $R_2=R_3=R$ for sorbitan diesters, $R_1=R_2=R_3=R$ for sorbitan triesters, where $R=$ ($C_{11}H_{23}$) COO for laurate, ($C_{17}H_{33}$) COO for oleate, ($C_{15}H_{31}$) COO for palmitate or ($C_{17}H_{35}$) COO for stearate.

18. The method of claim 11 wherein said surface active agent is polyoxyethylene stearate.

19. The method of claim 11 wherein said surfactant is polyoxyethylene sorbitan fatty acid ester of the formulas (1) and (2)

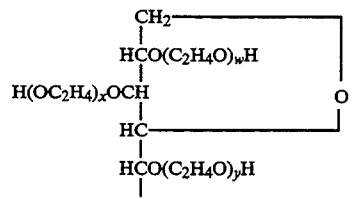

Polyoxyethylene sorbitan monoester

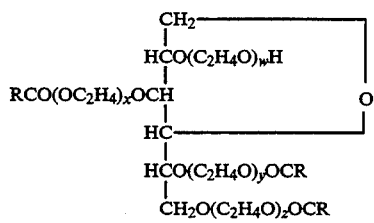

Polyoxyethylene sorbitan triester wherein
 $w+x+y+z=20$
 $w+x+y+z=5$
 $w+x+y+z=4$.

20. The method of claim 11 wherein said x-ray producing agent is selected from the group consisting of: N-acetyl-N-2-octyl-4-iodoaniline or N-(4'-iodophenyl)-2-amino octane.

* * * * *